(12) United States Patent
Giovanoli et al.

(10) Patent No.: US 9,097,627 B2
(45) Date of Patent: Aug. 4, 2015

(54) PUNCHING DEVICE WITH RECEIVING PLATE

(75) Inventors: Nando Giovanoli, Bivio (CH); Reto Menzi, Filzbach (CH)

(73) Assignee: HAMILTON BONADUZ AG, Bonaduz (CH)

( * ) Notice: Subject to any disclaimer, the term of this patent is extended or adjusted under 35 U.S.C. 154(b) by 0 days.

(21) Appl. No.: 14/113,911

(22) PCT Filed: Apr. 29, 2012

(86) PCT No.: PCT/EP2012/057873
§ 371 (c)(1),
(2), (4) Date: Oct. 25, 2013

(87) PCT Pub. No.: WO2012/146771
PCT Pub. Date: Nov. 1, 2012

(65) Prior Publication Data
US 2014/0056762 A1    Feb. 27, 2014

(30) Foreign Application Priority Data
Apr. 29, 2011    (DE) .......................... 10 2011 075 037

(51) Int. Cl.
*G01N 1/08*    (2006.01)
*G01N 1/28*    (2006.01)
(Continued)

(52) U.S. Cl.
CPC ................ *G01N 1/286* (2013.01); *G01N 35/04* (2013.01); *G01N 1/08* (2013.01); *G01N 2001/288* (2013.01); *G01N 2035/00148* (2013.01); *G01N 2035/0477* (2013.01)

(58) Field of Classification Search
CPC ............ G01N 1/04; G01N 1/286; G01N 1/08
USPC ......................................... 73/864.41; 422/63
See application file for complete search history.

(56) References Cited

U.S. PATENT DOCUMENTS 5,638,170 A    6/1997    Trinka et al.
5,641,682 A    6/1997    Pagels et al.
(Continued)

FOREIGN PATENT DOCUMENTS

CN    1965224 A    5/2007
DE    689 07 958 T2    1/1994
(Continued)

OTHER PUBLICATIONS

Chen et al., "Automatic tissue arrayer and method for reliable and rapid construction of tissue microarray (TMA) blocks", Scientific Research and Essays, vol. 5 (19), Oct. 4, 2010, pp. 3032-3043.
(Continued)

*Primary Examiner* — Paul Hyun
(74) *Attorney, Agent, or Firm* — Rothwell, Figg, Ernst & Manbeck PC

(57) ABSTRACT

A punching device is provided for processing samples applied to a sample card comprising at least one punching head with a punch and a lower die, the punch being movable between a resting position and a punching position. The punching head has a receiving opening into which a sample card can be introduced by a movable gripping unit, and a punching drive, which drives the movement of the punch between the resting position and the punching position. A piece of sample punched out from the sample card can be discharged at an outlet opening of the lower die into a receiving recess of a receiving container. The punching device has a receiving plate, which forms a cover of an outwardly sealed housing for a drive unit, by which a transport frame resting on the receiving plate is moved in a plate plane relative to the punching head.

17 Claims, 8 Drawing Sheets

(51) Int. Cl.
 *G01N 35/04* (2006.01)
 *G01N 35/00* (2006.01)

(56) References Cited

U.S. PATENT DOCUMENTS

| | | | |
|---|---|---|---|
| 8,920,721 B2 | 12/2014 | Philippon et al. | |
| 2005/0196320 A1* | 9/2005 | Veiner et al. | 422/63 |
| 2008/0063562 A1 | 3/2008 | Hoover et al. | |
| 2009/0097948 A1 | 4/2009 | Zuppiger et al. | |
| 2011/0034343 A1 | 2/2011 | Erling et al. | |
| 2011/0132111 A1* | 6/2011 | Shoemaker et al. | 73/864.41 |
| 2011/0150611 A1 | 6/2011 | Philippon et al. | |

FOREIGN PATENT DOCUMENTS

| | | |
|---|---|---|
| DE | 600 28 352 T2 | 3/2007 |
| DE | 699 32 607 T2 | 10/2007 |
| EP | 0 753 747 A2 | 1/1997 |
| WO | 2005/093433 A1 | 10/2005 |
| WO | 2009/029696 A1 | 3/2009 |
| WO | 2010/009173 A1 | 1/2010 |
| WO | 2010001023 A2 | 1/2010 |

OTHER PUBLICATIONS

International Search Report from PCT/EP2012/057873 dated Jul. 19, 2012, 3 pgs.
German Search Report from 10 2011 075 037.1 dated Apr. 14, 2012, 8 pgs.
Notice of Reasons for Rejection issued in copending Japanese Patent Application No. 2014-506905, 15 pages (Oct. 6, 2014).
Office Action with English Translation in copending Chinese Patent Application No. 2012800207504, 12 pages (Jan. 28, 2015).
Search Report issued in copending Chinese Patent Application No. 2012800207504, 2 pages (Jan. 15, 2015).

* cited by examiner

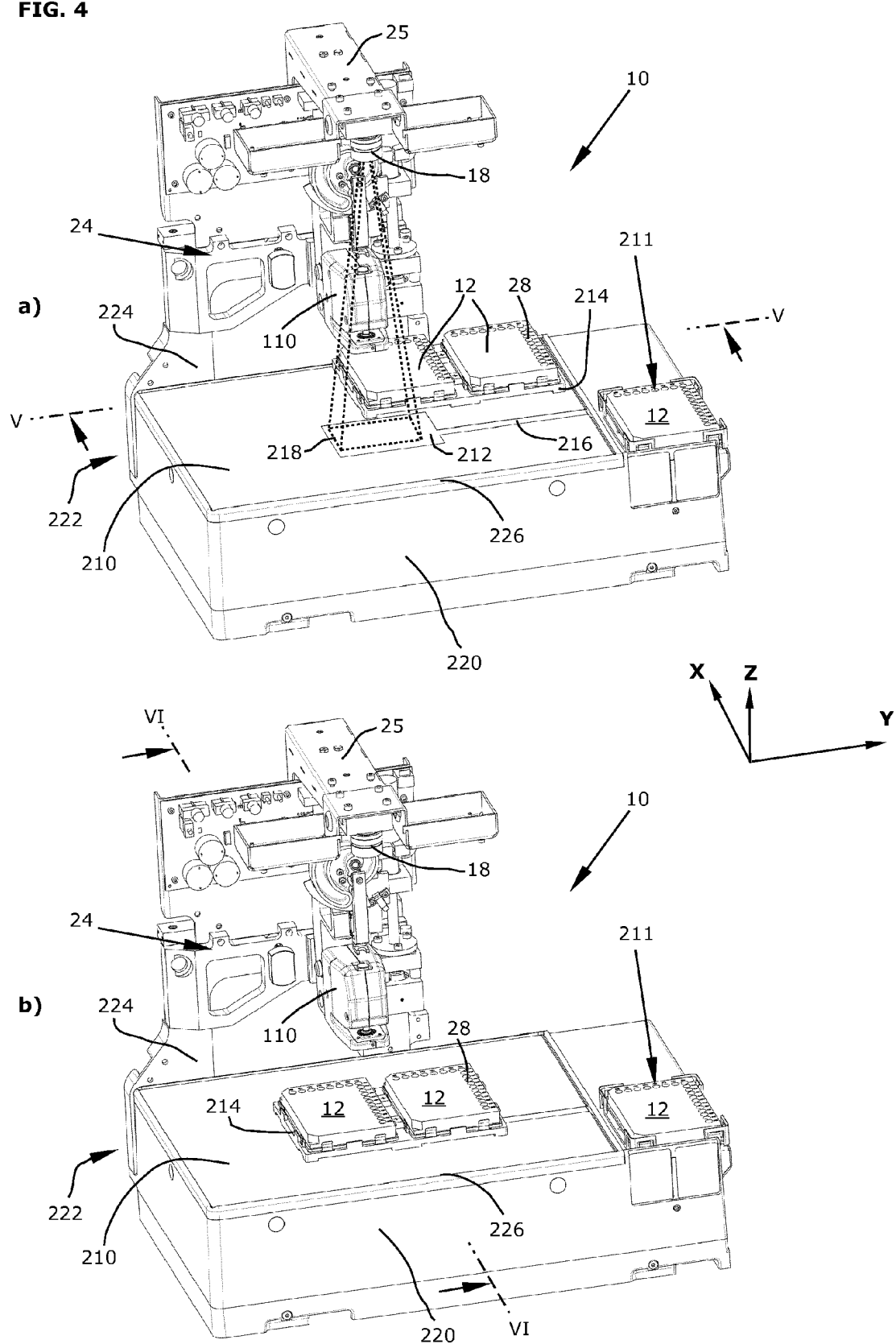

US 9,097,627 B2

PUNCHING DEVICE WITH RECEIVING PLATE

CROSS REFERENCE TO RELATED APPLICATION

This application is a 35 U.S.C. 371 National Phase Entry Application from PCT/EP2012/057873, filed Apr. 29, 2012, which claims the benefit of German Patent Application No. 10 2011 075 037.1 filed on Apr. 2011, the disclosure of which is incorporated herein in its entirety by reference.

The present invention relates to a punching device for processing dried samples applied to a sample card, in particular of liquids containing DNA such as blood, saliva and the like.

In such punching devices, a plurality of sample cards are kept in a magazine for sample cards and are removed from the magazine in a particular order by means of a gripper unit and fed to a punching means of the punching device. In an area, previously captured by means of imaging methods, in which the applied sample has been identified on the sample card, at least one sample piece is then punched out of the sample card. It is also possible for a plurality of sample pieces to be punched simultaneously or in succession out of the same sample area. The punched out sample pieces are guided through an outlet opening in a lower die by the movement of a punching pin (punch) and in this way transported into a receiving recess in a receiving container, preferably into a well of a microtiter plate. As soon as sample pieces have been punched out of all the desired sample cards and have been received in the receiving container, the analysis of the individual samples contained in the sample pieces can take place by means of methods such as PCR for DNA analyses, high-performance gas chromatography (HPLC) or the like, wherein, for this purpose, further steps, which are not described in detail in the scope of the present application, are carried out after punching out.

A method and a device for automatically punching sample pieces out of sample cards is known for example from U.S. Pat. No. 5,641,682.

Furthermore, a punching device of the abovementioned type is known under the designation "BSD1000-GenePunch" from BSD Robotics (a Luminex Company, in Brisbane, Queensland 4110, Australia). An associated product flyer was available at the following Internet address at the time that the present application was filed: http://www.bsdrobotics.com/Documents/Brochure/BSDR1000(10)%20-%20BSD1000%20GenePunch.PDF.

Furthermore, the mode of operation of this punching device is disclosed in a video film which was available at the following Internet address at the time the application was filed: http://www.bsdrobotics.com/Videos/BSD1000.wmv.

The following mode of operation can be seen from the video film: In the "BSD1000-GenePunch" punching device, a gripper device for sample cards is moved from a magazine, from which the gripper device has removed a sample card, along a horizontally extending rail to a scanner into which the sample card is introduced and subsequently scanned. The gripper device is in this case movable in two directions which are orthogonal to one another, specifically along the rail and orthogonally to the latter, such that the grasped sample card is movable in two dimensions in its card plane. After scanning, the sample card is transported by means of the gripper device to the punching means of the punching device and positioned relative to said punching means, in order that a sample piece can be punched out at that position of the sample card that is evaluated after scanning. The punched-out sample piece is subsequently dispensed into a receiving container, for instance a well of a microtiter plate, arranged under the punching means. In the case of this punching device, a plurality of receiving containers are arranged in a star shape around a rotation axis orthogonal to a horizontal plane, and the position thereof, in particular of a particular well, relative to the punching means takes place by means of a rotary movement and by means of displacement in the horizontal plane. After the punching of one or more sample pieces out of a sample card has been completed, the gripper device transports the punched sample card back along the rail to the card magazine and sets it down there again. The gripper device is then briefly pulled back until the card magazine has been moved upward by one position in order to be able to remove the next sample card from the magazine.

In general terms, a punching device known from the prior art thus comprises at least one punching means having a punch and a lower die, wherein the punch is movable between a rest position in which it is away from the lower die and a punching position in which it is close to the lower die, and wherein the punching means has a receiving opening into which a sample card is introducible by means of a movable gripper unit of the punching device and is positionable relative to the punching means, and a punching drive which is couplable or coupled to the punch of the punching means and by way of which the movement of the punch between the rest position and the punching position is driven, wherein the punching means is set up such that a sample piece punched out of the sample card can be dispensed at an outlet opening of the lower die into a receiving recess in a receiving container arranged beneath the punching means.

With such punching devices, there is the problem that dust particles are produced during the punching operation and said dust particles can be deposited on the punching device, in particular on components located underneath the punching means, for example the star-shaped rotation unit of the above-described punching device BSD-1000. This can result in soiling, in particular at drives, and this makes relatively frequent maintenance necessary.

It is the object of the invention to develop a punching device of the abovementioned type such that improved protection against dust particles can be achieved.

In order to achieve the object, it is proposed that the punching device has a receiving plate which forms a cover of a housing, sealed toward the outside, for a drive unit by way of which a transport frame resting on the receiving plate is moved in the plate plane relative to the punching means.

The receiving plate creates a structural separation between the drive for the transport frame and the punching means that is arranged above the latter and generates dust particles. Dust particles which occur are not deposited on the drive for the transport frame but rather on the receiving plate, which can be cleaned easily. By accommodating the drive unit in a sealed-off housing, which is upwardly covered with respect to the punching means by means of the receiving plate, soiling of the drive with dust particles from the ambient air can be virtually completely prevented, this having an advantageous effect on maintenance.

At least one receiving container can be received in the transport frame in order to be able to move and position the receiving container on the receiving plate relative to the punching means by means of the transport container.

In a development, it is proposed that the transport frame is coupled in a contactless manner by means of magnets to the drive unit covered by the receiving plate.

In this case it is preferred for the drive unit located in the housing to be configured such that the transport frame is movable in two main directions, which are orthogonal to one another, of the plate plane.

The magnetic coupling between the drive unit and the transport frame allows sufficiently precise positioning of the transport frame or of a receiving container received therein relative to the punching means. Preferably, the transport frame is coupled to the drive unit at a plurality of points via individual magnets, so that the relative movement between the drive unit and the transport frame can be kept as small as possible in order to prevent serious errors in the positioning of the transport frame.

It is furthermore proposed that a parking receptacle is provided adjacent to the receiving plate, a receiving container to be processed being positionable on said parking receptacle by means of the gripper unit prior to or after being loaded with punched out sample pieces.

The punching device may have various storage areas in which at least one sample card container, which contains a plurality of sample cards, or/and at least one receiving container are positionable in order to be processed by means of the stamping device, wherein the storage areas are set up such that sample card containers located therein or the contained sample cards or/and receiving containers located therein are accessible by the gripper unit.

Receiving containers can be transported by means of the gripper unit from waiting positions in a corresponding storage area outside the receiving plate to processing positions on the receiving plate and vice versa.

In this case, it is preferred for the gripper unit to be configured such that receiving containers can be moved toward and away from the transport frame by means of the gripper unit.

In a development, it is proposed that the punching device furthermore has a light source illuminating at least a part of a receiving plate, wherein the light source is arranged such that at least a part of a receiving container located on the receiving plate, in particular receiving recesses provided in said receiving container, can be illuminated from the direction of the receiving plate, in particular from below.

In this case, at least one electroluminescent film may be provided as light source on the receiving plate, wherein preferably the receiving plate is a transparent plate, preferably a glass plate, and wherein the EL film is arranged preferably on the underside of the receiving plate.

The invention is described in the following by way of example and in a nonlimiting manner with reference to the appended figures.

FIG. 4 shows, in partial figures a) and b), perspective views of the punching device, wherein in partial figure b) receiving containers are arranged in the region of a light source.

Figure 1:
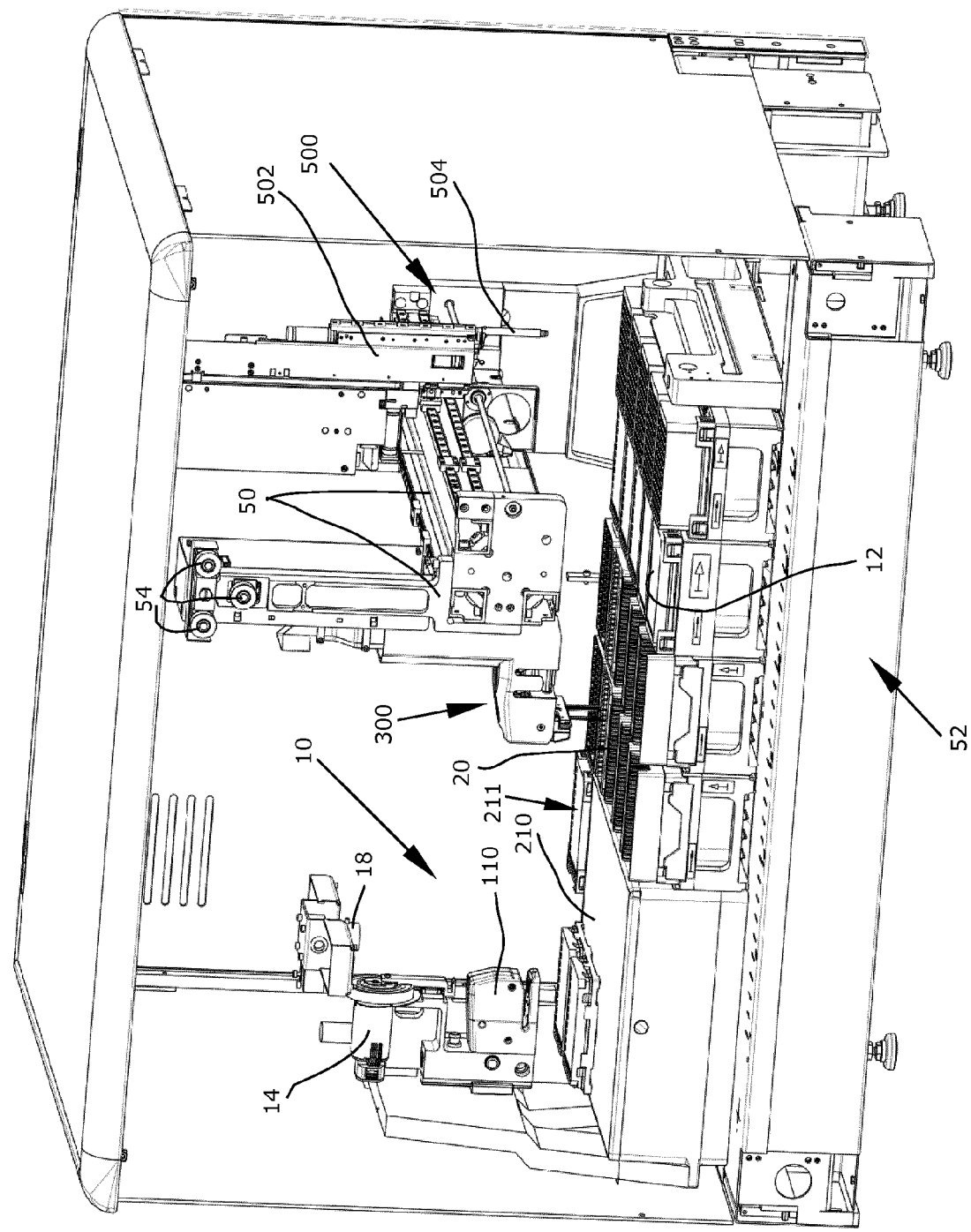
FIG. 1 shows a schematic perspective illustration of a punching device in combination with a metering device.

FIG. 1 shows an overall view of a punching device 10, which is optionally combined here with a metering device 500. In the combination illustrated here, the punching device 10 and the metering device 500 use a common support 50 which is movable in one of the main directions X, Y, Z, namely in the longitudinal direction X. To this end, the support 50 is mounted by means of rollers 54 on longitudinal rails (not illustrated), in the upper region of a support structure 52 which is provided for the overall device but only illustrated in part here. Of course, a drive device (not illustrated) for the support 50 is also present, said drive device being actuable via a control unit (likewise not illustrated) of the overall device.

The metering device comprises a pipetting device 502, fitted on the support 50 so as to be movable in the two other main directions Y, Z, that is to say the transverse direction Y and the vertical direction Z, having at least one pipetting channel 504 for drawing and dispensing liquid into/out of provided receiving containers 12 or a reservoir for the liquid to be metered. The metering device 500 is configured as an automated pipetter, known per se, and will not be described in further detail here.

Fitted on that side of the support 50 that is opposite the pipetting device 502 is a gripper unit 300 which is likewise configured to be movable in the two other main directions Y, Z. This gripper unit 300 should be considered, in the scope of this application, as belonging to the punching device 10, even if in the present example it is fitted on a support 50 that is used jointly with the pipetting device 502. Furthermore, the punching device 10 comprises, as further main components, a punching drive 14, a punching means 110, an image capturing device 18 and a receiving plate 210. Furthermore, magazines 20 for in each case a plurality of sample cards 22 (FIG. 3) can be seen in FIG. 1. By means of the gripper unit 300, a sample card is removed from a magazine 20 and fed to the punching means 110, so that by means of the punching means 110 at least one sample piece can be punched out of the respective sample card.

The function of the modular punching means 110, which, due to its self-contained structure, can be easily separated from the punching device 10, is described only in part in the scope of this application. For details concerning the configuration of the modular punching means (punching head) 110, reference is made to the application, filed simultaneously by the applicant, having the title "Punching device having a modular punching means" (application number DE102011XXXXXX.X), the content of which is incorporated here by reference with respect to the configuration of the punching means.

The function of the gripper unit 300 is likewise described only in part in the scope of this application. For details concerning the configuration of the gripper unit and the interaction thereof with the punching device or the punching means of the present application, reference is made to the application, filed simultaneously by the applicant, having the title "Punching device having a gripper unit" (application number DE102011XXXXXX.X), the content of which is incorporated here by reference with respect to the configuration of the gripper unit.

Figure 2:
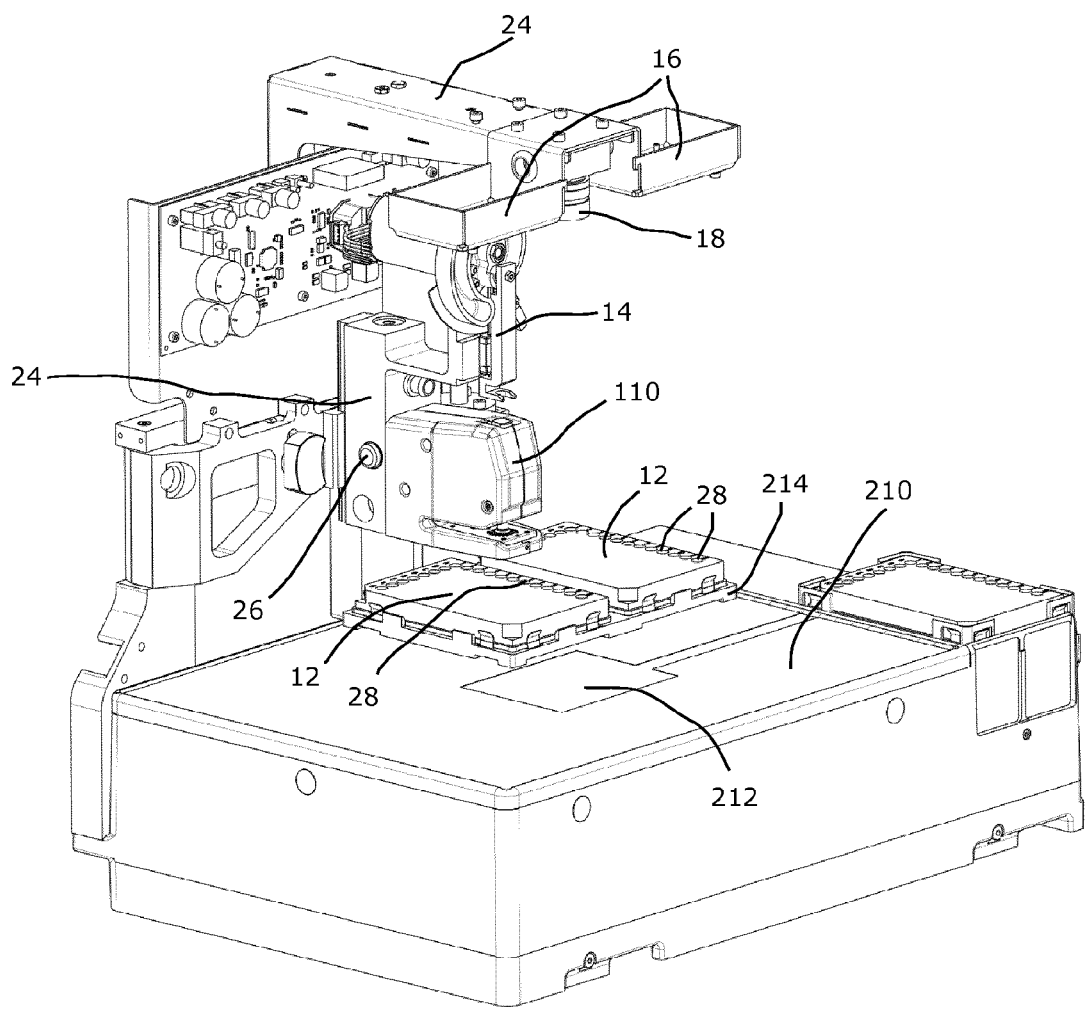
FIG. 2 shows a schematic perspective illustration of the punching device without a metering device and without a gripper unit.

FIG. 2 shows a schematic perspective illustration of the punching device 10 without a gripper unit 300. The punching device 10 comprises a frame-like structure or support structure 24, to which the punching drive 14 and the image capturing device 18 are fastened, and on which the punching means 110 is fitted in a removable manner as a punching means module. FIG. 2 shows the state in which the modular punching means 110 is coupled to the structure 24 of the punching device. In order to be able to remove the punching means 110 from the structure 24, it is proposed that an actuating element or push button 26 can be actuated so that an engagement between the punching means 110 and the support structure 24 can be released. The receiving plate 210 serves for mounting or supporting at least one receiving container 12, which is preferably provided as a microtiter plate having a particular number of wells (receiving recesses) 28. It is also possible for different microtiter plates to be used, and the number of wells 28 is not limited per se, except with regard to the fact that a sample piece punched out of a sample card has space in a corresponding well 28.

It is also apparent from the overview illustration in FIG. 2 that the image capturing device 18 is arranged substantially vertically above an illuminated area 212 of the receiving plate 210. This illuminated area 212 is formed preferably by an electroluminescent film received in the receiving plate or arranged on the rear side thereof. A microtiter plate 12 arranged thereon can be backlit by the EL film 212, such that an image of the backlit microtiter plate 12 or of a part thereof can be captured by the image capturing device 18. The microtiter plate(s) 12 is/are received on the receiving plate 210 in a transport frame 214 which is coupled via magnets (not illustrated here) to a drive unit located under the receiving plate 210 and can be moved on the receiving plate 210 relative to the stationary punching means 110 by means of this drive unit. As a result, a particular receiving recess 28 of a receiving container 12 can be arranged precisely beneath the punching means 110, such that a punched-out sample piece drops into this receiving recess or is received in the latter. Provided on both sides of the image capturing device 18 are holders 16 for alternative illumination means, which illuminate from above an article, preferably a sample card, positioned under the image capturing means 18, so that image-processing processes can be carried out for the sample card, for example recognition of a bar code or the like.

Figure 3A:
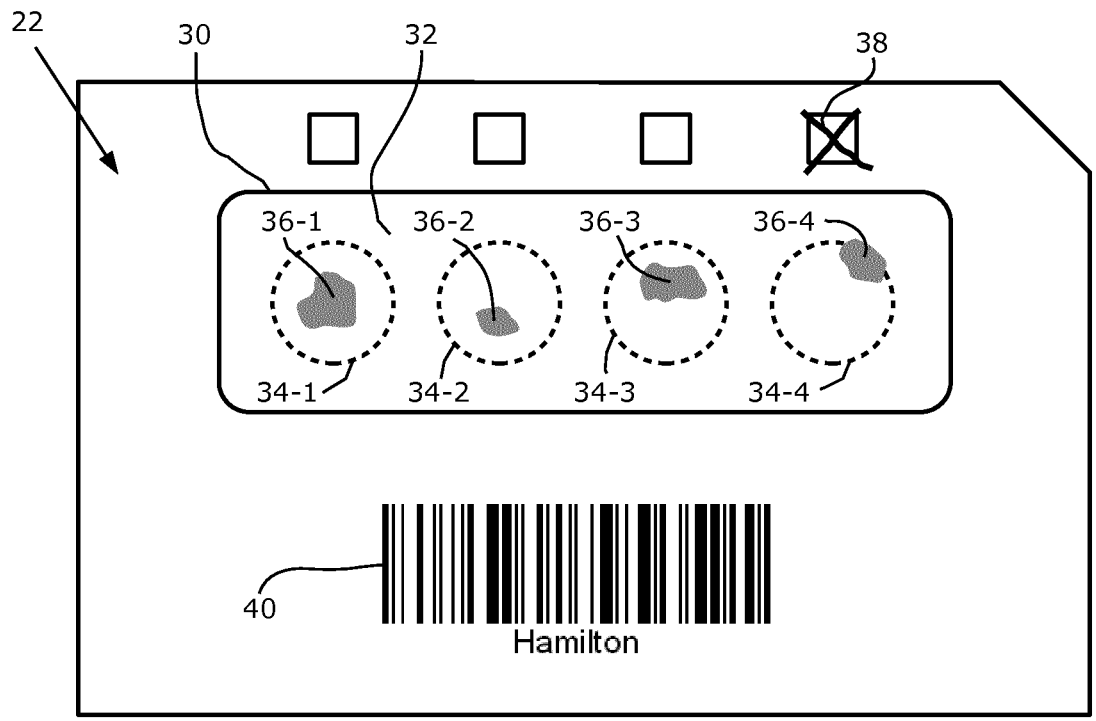
FIG. 3 shows, in partial figures a) and b), schematically illustrated sample cards in the state prior to the punching out of sample pieces (FIG. 3a) and after the punching out (FIG. 3b).
Figure 3B:
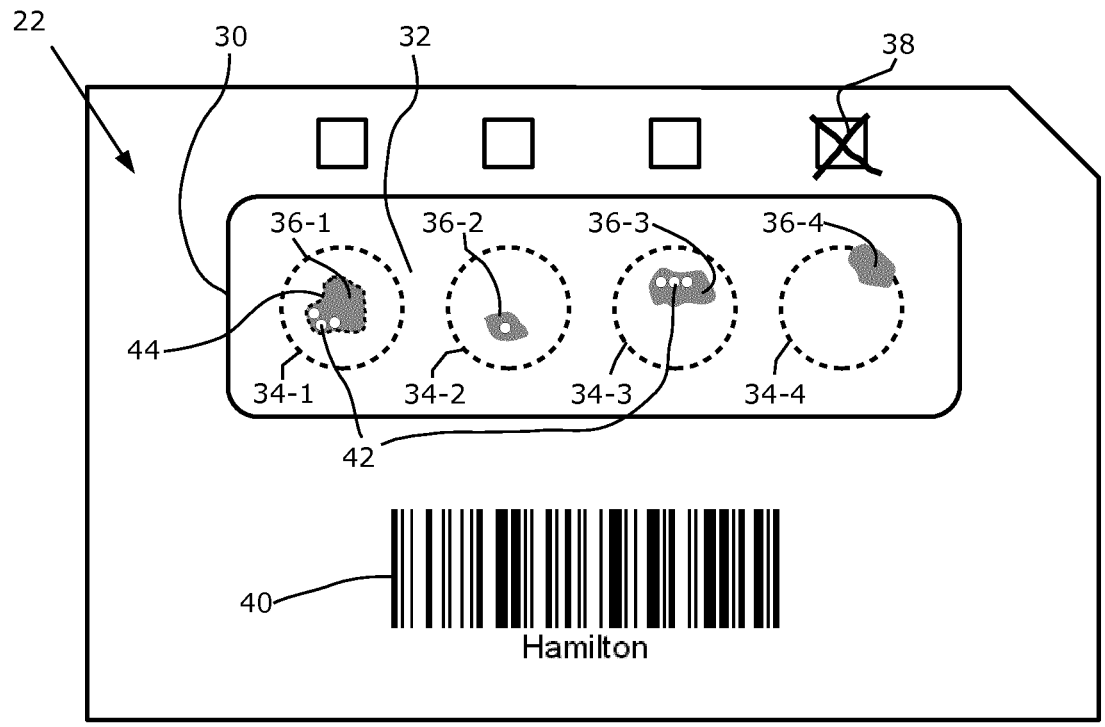

FIG. 3 shows, in partial figures a) and b), an example of a sample card 22. The sample card has a kind of opening 30, in which an absorbent material 32, for instance a kind of filter paper or the like is visible. At least one sample area is identified on the absorbent material, and in the present case there are four such sample areas 34-1 to 34-4, which are illustrated as dashed circles. If samples, such as blood, saliva or other liquids are collected by means of the sample card 22, the liquid samples are intended to be deposited as far as possible within the marked sample areas 34-1 to 34-4. In the present example, samples 36-1 to 36-4 of different sizes, for example drops of blood or samples of saliva, have been deposited in the corresponding sample areas 34-1 to 34-4. The sample 36-4 is in this case not located completely within the marking of sample area 34-4, and so this sample has correspondingly been indicated as invalid by a sample donor or by a member of medical staff by way of a cross 38 above the sample area 34-4. A code (bar code, 2D bar code or the like) 40 is also provided on the card beneath the absorbent material 32, in order to allow the sample card to be identified and to be assigned to a sample donor, a collecting institute or the like. Further information, such as manufacturer's information, information regarding the purpose of the card or regarding the sample liquid, etc. may also be contained or printed on the sample card 22. The samples 36-1 to 36-4 applied in liquid form are absorbed by the absorbent material 32 and subsequently dry. After drying, sample pieces can be punched out of the samples 36-1 to 36-4 by means of the punching means 110. After a plurality of sample pieces have been punched out of the samples 36-1 to 36-3, the sample card 22 is indicated in FIG. 3b by the white punched holes 42. Where and in what order sample pieces are punched out can be established for example by means of image processing, wherein it is firstly possible to detect whether a sample is located within the marked sample area 34-1 to 34-4 (for example by using the cross 38), where the sample 36-1 to 36-4 is located within the sample area 34-1 to 34-4, and what boundary it has, this being indicated by the dashed line 44 in the case of the sample 36-1. Using such information and the desired number of sample pieces to be punched out, it is possible to identify where sample pieces should be punched out. Accordingly, the sample card 22 can then be positioned relative to the punching means so that the sample pieces can be punched out at the predetermined points. The form illustrated here of the sample card is purely by way of example, and the sample card can have some other format, more or fewer, smaller or larger sample areas 34, etc.

FIG. 4 shows, in partial figures a) and b), the punching device 10 having the movable transport frame 214 which is arranged on the receiving plate 210 and on which by way of example two receiving containers 12 are arranged. In FIG. 4a), the transport frame is in a position in which it is not arranged on the light source 212. In FIG. 4b), the transport frame is positioned over the light source 212 so that the receiving container 12 can be illuminated from below by the light source 212. The light source 212, which is preferably configured as an electroluminescent film, is located at least partially in the field of view 218, indicated by dashed lines, of the image capturing device 18, which is arranged substantially vertically above the light source 212. The image capturing device 18 is arranged in the X direction on the support 25 of the support structure 24 of the punching device 10 such that the field of view 218 is not impaired by the punching means 110 arranged underneath. The EL film 212 is connected via a connection 216 to an associated, not illustrated power source and controller, for instance an inverter or the like. Provided at 211 is a waiting or transfer position next to the receiving plate 210, at which one or more receiving containers 12 can be temporarily stored prior to or after punching.

The receiving plate 210 is produced preferably from a transparent and in particular wear-resistant material, for instance glass or a plastics material suitable therefor. The receiving plate 210, on which the transport frame 214 can be moved in a sliding manner, is simultaneously also the cover of a box-like housing 220, on the rear side 222 of which, with regard to the viewing direction of FIG. 4, a support 224 of the supporting structure 24 of the punching device 10 is fitted. The receiving plate 210 has an encircling plate rim 226 supporting it. Within this boundary 226, the transport frame 214 can be moved, by means of a drive unit 230 (not visible in FIG. 4) accommodated in the housing 220, into any desired position on the receiving plate 210.

Figure 5:
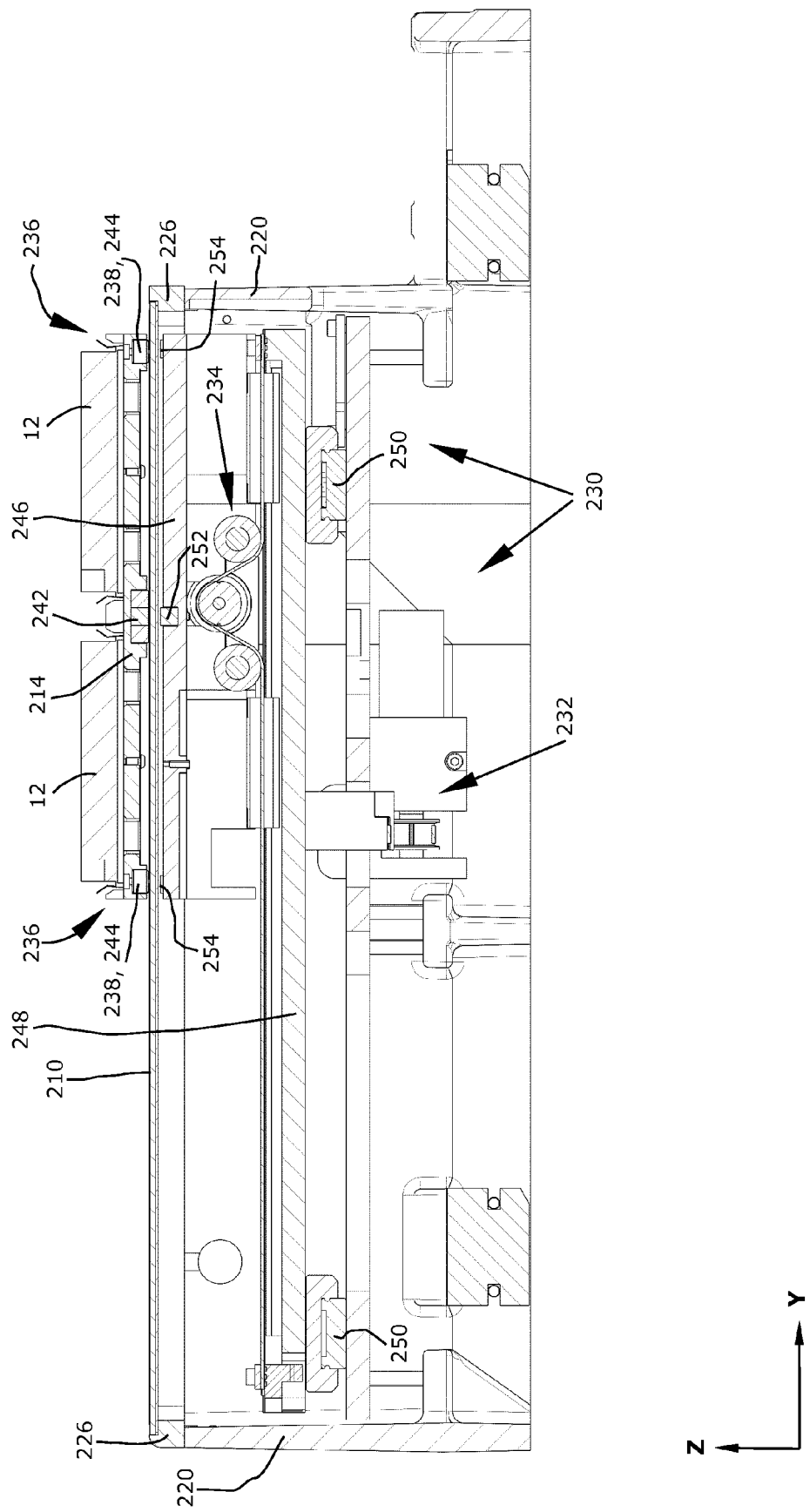
FIG. 5 shows a sectional illustration, corresponding to the section line V-V in FIG. 4a, of a housing and a drive unit, accommodated therein, for moving receiving containers on a receiving plate covering the housing.
Figure 6:
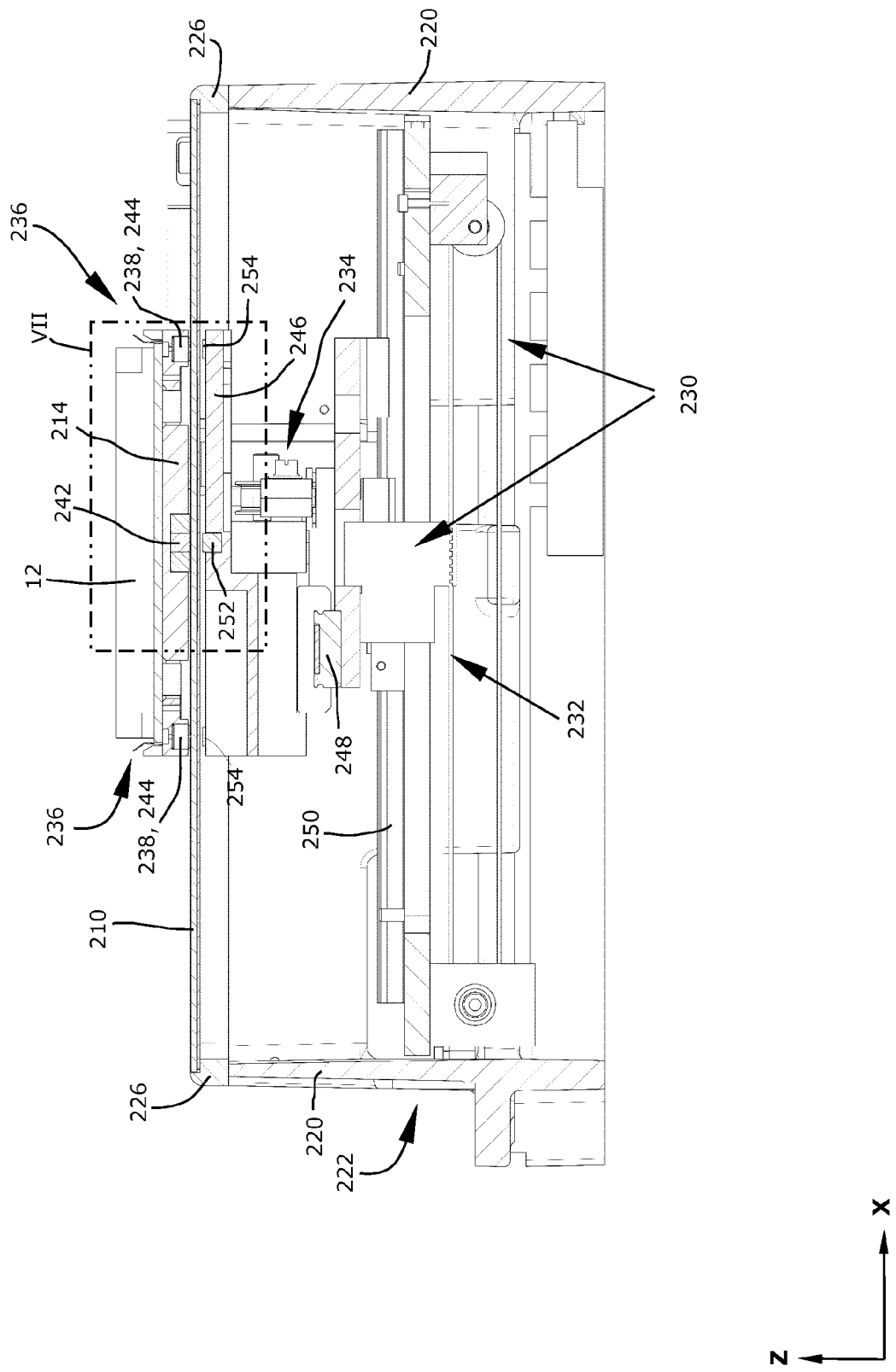
FIG. 6 shows a sectional illustration, corresponding to the section line VI-VI in FIG. 4b, of the housing and the drive unit, accommodated therein, for moving receiving containers on the receiving plate.
Figure 7:
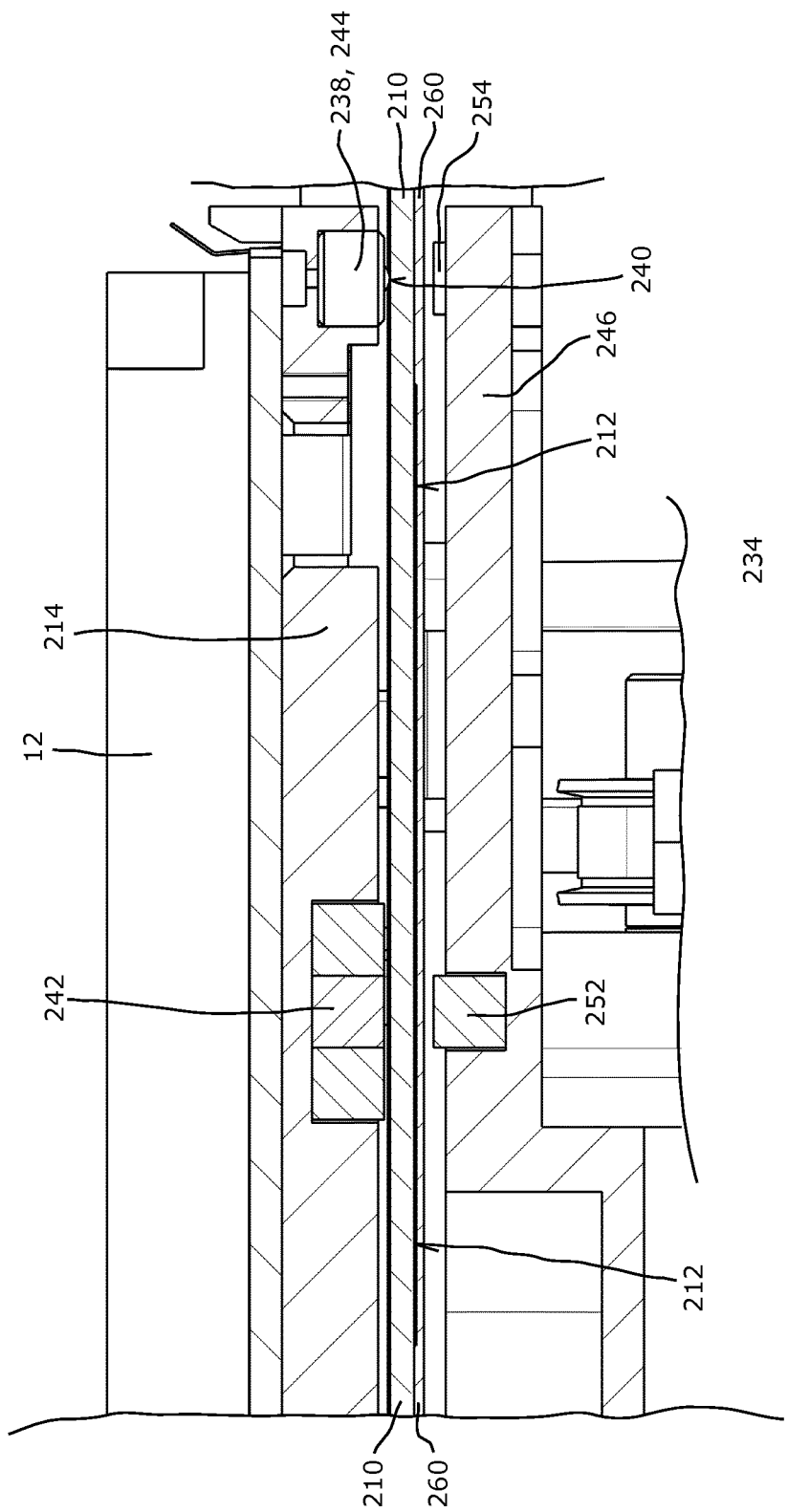
FIG. 7 shows an enlargement of the region VII marked in FIG. 6 by way of a dashed rectangle.

The drive unit 230 is described in the following text with reference to the sectional illustrations in FIGS. 5 to 7. The drive unit 230 comprises two separate drives 232, 234, which are set up for moving the transport frame 214 in the X direction (drive 232) and the Y direction (drive 234). In its corner regions 236, the transport frame 214 has supporting feet 238, on which there is arranged a spherical or spherical-cap-shaped sliding element 240 which rests on the receiving plate 210 (FIG. 7). The form of the sliding elements 240 allows the transport frame 214 to rest in a point-wise manner at its four corners 236 on the receiving plate 210, so that the frictional resistance between the transport frame 214 and the receiving plate 210 can be kept as low as possible. In a central region of the transport frame 214, a coupling magnet 242 can be seen, which is arranged a short distance above the receiving plate 210. Further coupling magnets 244 can also be provided in the region of the supporting feet 238, and preferably the supporting feet 238 or/and the sliding elements 240 themselves serve as coupling magnets 244.

Beneath the receiving plate 210, a drive frame 246 located opposite the underside of the transport frame 214 is provided within the housing 220 of the drive unit 230, said drive frame 246 being supported on a rail-like support 248 and being able to be moved in the Y direction along this support 248 by means of the drive 234. On its top side, the drive frame 246 has a plurality of coupling magnets 252, 254 which are arranged such that they are operatively connected to the coupling magnets 242, 244 of the transport frame 214, such that magnetic coupling is enabled between the drive frame 246 and the transport frame through the receiving plate 210. Due to this contactless, magnetic coupling between the drive frame 246 and the transport frame 214, the transport frame 214 resting on the receiving plate 210 follows the movement or movements of the drive frame 246 beneath the receiving plate 210.

The rail-like support 248 is for its part supported on the sliding rails 250 arranged orthogonally thereto and is connected to the drive 232 so that the support 248 can be moved in the X direction along the sliding rails 250 by means of the drive 234. Thus, the drive 232 for the Y direction can likewise be moved in the X direction due to its coupling to the support 248 that is movable in the X direction, and so the drive frame 246 can also execute superposed movements in both directions X and Y. Belt drives are illustrated by way of example here for the drives 232 and 234. However, other drives may also be suitable, for instance a spindle drive, linear motor or the like. The drive unit 230 having the drives 232 and 234 is protected toward the outside by the housing 220 and the receiving plate 210 and it is possible to prevent penetration of dust particles which arise during punching and which can generally not be completely removed by a suction-extraction device provided on the punching means 110 (FIG. 4).

The enlarged sectional illustration of FIG. 7 furthermore shows the light source 212, in the preferred form of an electroluminescent film 212, fitted on the underside of the receiving plate 210. Otherwise, the receiving plate 210 furthermore has on its underside a further plate or coating 260, wherein the EL film 212 is received preferably between the receiving plate 210 and this plate/coating 260. The receiving plate 210 is preferably configured in a transparent manner, and the plate/coating 260 can be produced from a non-transparent or opaque material, in order that it is not possible to look into the housing 220 and see the drive unit 230. As a result, a neutral background can be created for the image capturing device 18 over the entire surface of the receiving plate 210. Alternatively, however, the plate/coating 260 can also be transparent. If the EL film 212 is made to light up, its light radiates upwardly (in the Z direction) through the receiving plate 210, so that an article arranged above it, for instance a receiving container 12 located in the transport frame 214 or a sample card 22 (FIG. 3) held by the gripper unit 300 (FIG. 1), is illuminated from below.

Figure 8:
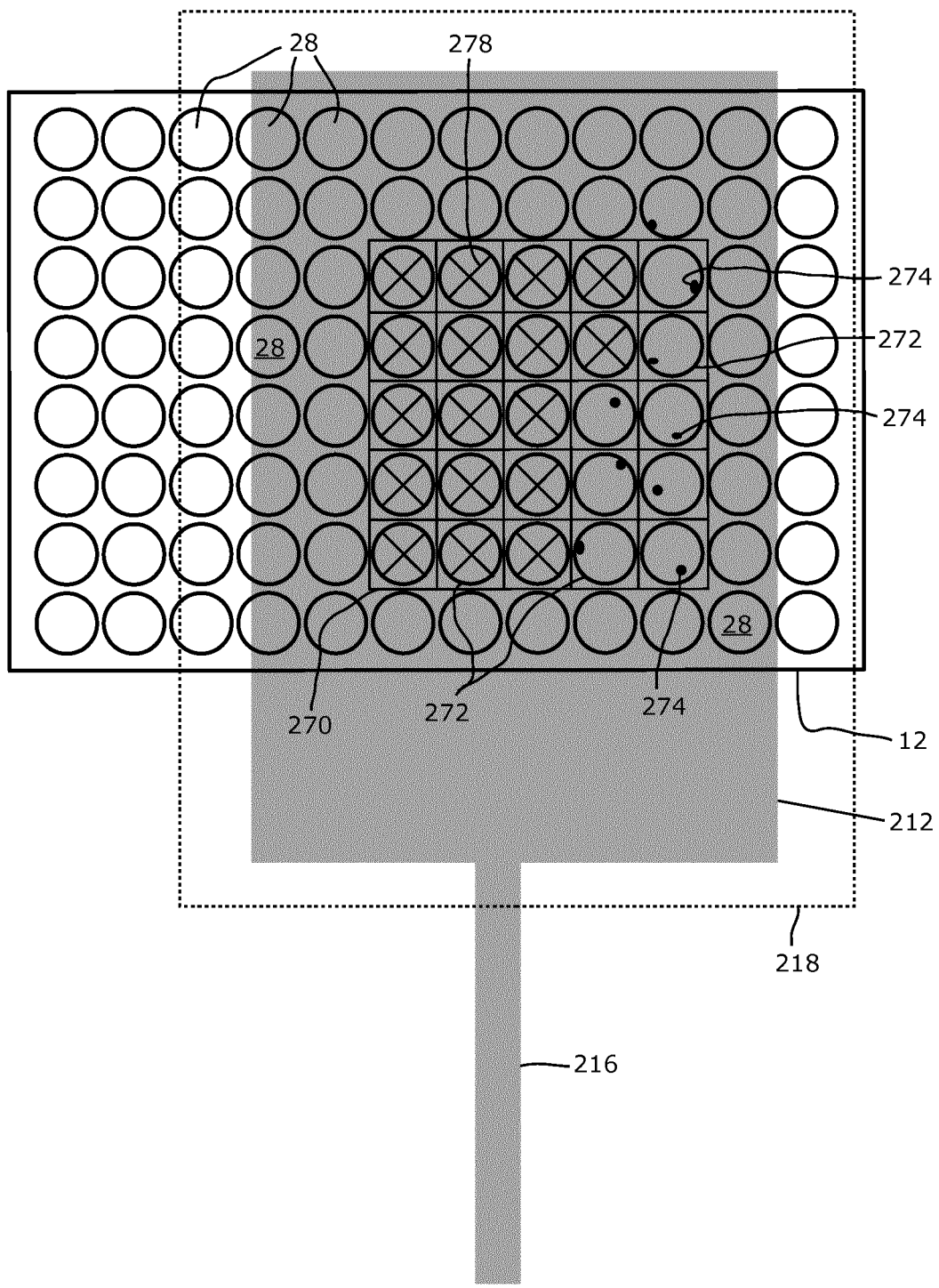
FIG. 8 shows a schematic and highly simplified illustration of a plan view of a receiving container backlit by a light source and possible evaluation areas for an analysis method.

This illumination from below, which is also known as backlighting, is illustrated in a highly simplified and schematic manner in FIG. 8. FIG. 8 shows a plan view of the receiving container 12 with its receiving recesses 28. This may be a microtiter plate 12 with its wells 28. The receiving container 12 is arranged at least partially over the EL film 212, which is illustrated gray here. The receiving recesses 28 of the preferably transparent receiving container 12 are illuminated from below by the EL film 212, so that its light passes through the receiving recesses 28. An image of the receiving container 12 or at least a part of the latter can be captured by means of the image capturing device 18 (FIG. 4) within its field of view 218. The outlines 272 of the receiving recesses 28 can be detected and positions thereof determined by image processing for example in an analysis region 270 specified for example by the image processing software or by the user. Furthermore, sample pieces 274 contained in the receiving recesses 28 and punched out of sample cards can be detected, said sample pieces 274 appearing as dark, point-like regions due to the backlighting by the EL film 212. By way of the image processing, it is furthermore possible to identify or check an assignment of sample pieces 274 to particular receiving recesses 28. By including data about the positioning of the receiving container 12 relative to the stationary image capturing device 18, it is possible to determine which receiving recesses 28 of the receiving container 12 should be located in the analysis region 270. It is possible to display for example an image captured by the image capturing device 18 together with the analysis region 270 on a monitor connected to the control device of the punching device 10. It is then possible to mark and visualize for example detected but still empty receiving recesses 28 in this display by way of a cross 278.

Of course, it is also possible to check for the presence of punched holes 42 (FIG. 3) in a sample card 22 with the image capturing device and the image processing, with the sample card likewise being illuminated from below by the EL film 212 for this purpose. Punched-out holes then appear in an image captured by the image capturing device as point-like regions in the color of the light emitted by the EL film 212. From a combination of FIGS. 8 and 3b, this would mean that the punched holes 42 illustrated white in FIG. 3b would be illustrated gray in FIG. 8, when the sample card has been positioned over the EL film 212 by means of the gripper unit 300.

The embedding of an EL film 212 in the receiving plate 210 thus makes it possible to carry out different analytical method steps in order to be able to establish whether everything has proceeded correctly during the punching out of sample pieces from the sample cards and during the introduction of these sample pieces into a particular receiving recess. The movement of the receiving container 12 from a position beneath the punching means 110 to a position on the EL film 212 and beneath the image capturing device 18 can take place for example at the time when a sample card which has just been punched is transported back to a magazine and set down there by the gripper unit 300. Thus, the period of time during which a punched sample card is transported away from the punching means to a magazine and a new sample card is transported from a magazine to the punching means can be used to simultaneously check whether the sample piece which has just been punched out has arrived in the correct (predetermined) receiving recess. If no sample piece can be detected in a receiving recess in which such a sample piece should be contained, it is possible to output an error message and to stop the automatic process. Such analysis options and steps increase the reliability in the correct assignment of sample pieces punched out of sample cards to the receiving recesses in the receiving containers. This minimizes the risk that results of an analysis, carried out automatically, of a sample piece are assigned to the wrong person as sample donor. The analysis steps mentioned here represent examples and should not be understood as limiting. It is clear that by combining data from different sources, for instance images, position sensors and the like, which can be captured by a control unit of the punching device 10 and optionally the metering device 500, further information can be obtained in order that an automatic punching process can be carried out.

The invention claimed is:

1. A punching device for processing dried samples applied to a sample card comprising
   at least one punching head having a punch and a lower die, wherein the punch is movable between a rest position in which the punch is away from the lower die and a punching position in which the punch is close to the lower die, and wherein the punching head has a receiving opening into which a sample card is introducible by a movable gripper unit of the punching device and the moveable gripper unit is positionable relative to the punching head, and a punching drive which is couplable or coupled to the punch of the punching head and is configured to drive the movement of the punch between the rest position and the punching position, wherein the punching head is set up such that a sample piece punched out of the sample card can be dispensed at an outlet opening of the lower die into a receiving recess in a receiving container arranged beneath the punching head, wherein the punching device has a receiving plate which forms a cover of a housing, sealed toward the outside, for a drive unit by way of which a transport frame resting on the receiving plate and coupled in a contactless manner is moved in a plate plane relative to the punching head.

2. The punching device as claimed in claim 1, wherein at least one receiving container is receivable in the transport frame.

3. The punching device as claimed in claim 1, wherein the contactless manner is by magnets to couple the transport frame to the drive unit covered by the receiving plate.

4. The punching device as claimed in claim 1, wherein the drive unit located in the housing is configured such that the transport frame is movable in two main directions, which are orthogonal to one another, of the plate plane.

5. The punching device as claimed in claim 1, wherein a parking receptacle is provided adjacent to the receiving plate, a receiving container to be processed being positionable on said parking receptacle by the gripper unit prior to or after being loaded with punched out sample pieces.

6. The punching device as claimed in claim 1, further comprising various storage areas in which at least one sample card container, which contains a plurality of sample cards, or/and at least one receiving container are positionable in order to be processed by a stamping device, wherein the storage areas are set up such that sample card containers located therein or the contained sample cards or/and receiving containers located therein are accessible by the gripper unit.

7. The punching device as claimed in claim 6, wherein receiving containers are transportable by the gripper unit from waiting positions in a corresponding storage area outside the receiving plate to processing positions on the receiving plate and vice versa.

8. The punching device as claimed in claim 7, wherein the gripper unit is configured such that receiving containers can be moved toward and away from the transport frame by the gripper unit.

9. The punching device as claimed in claim 1, further comprising a light source illuminating at least a part of the receiving plate wherein the light source is arranged such that at least a part of a receiving container located on the receiving plate can be illuminated from the direction of the receiving plate.

10. The punching device as claimed in claim 9, wherein the receiving recesses provided in said receiving container can be illuminated from the direction of the receiving plate.

11. The punching device as claimed in claim 9, wherein the direction of the receiving plate is from below.

12. The punching device as claimed in claim 9, wherein at least one electroluminescent film is provided as light source on the receiving plate.

13. The punching device as claimed in claim 12, wherein the receiving plate is a transparent plate.

14. The punching device as claimed in claim 13, wherein the transparent plate is a glass plate.

15. The punching device as claimed in claim 12, wherein the electroluminescent film is arranged on the underside of the receiving plate.

16. The punching device as claimed in claim 1, wherein the dried liquid samples includes bodily fluids.

17. The punching device as claimed in claim 16, wherein the bodily fluids includes at least one of blood and saliva.

* * * * *